United States Patent [19]

Ernst et al.

[11] Patent Number: 4,656,275

[45] Date of Patent: Apr. 7, 1987

[54] PREPARATION OF RIBOFLAVIN, AND 4,5-DIMETHYL-N-(D)-RIBITYL-2-(O-ALKOXYPHENYLAZO)-ANILINE INTERMEDIATES

[75] Inventors: Hansgeorg Ernst; Heinz Eckhardt, both of Ludwigshafen; Joachim Paust, Neuhofen, all of Fed. Rep. of Germany

[73] Assignee: BASF Aktiengesellschaft, Ludwigshafen, Fed. Rep. of Germany

[21] Appl. No.: 730,056

[22] Filed: May 3, 1985

[30] Foreign Application Priority Data

May 15, 1984 [DE] Fed. Rep. of Germany ....... 3417944

[51] Int. Cl.$^4$ .................. C07D 575/14; C07C 107/06
[52] U.S. Cl. ..................................... 544/251; 534/858
[58] Field of Search .......................... 544/251; 534/858

[56] References Cited

U.S. PATENT DOCUMENTS

| 2,237,074 | 4/1941 | Karrer ............................ 534/858 X |
| 2,350,376 | 6/1944 | Tishler et al. ....................... 544/251 |
| 2,370,093 | 2/1945 | Tishler et al. ................... 544/251 X |
| 2,807,611 | 9/1957 | Howe ................................ 544/251 |

FOREIGN PATENT DOCUMENTS 3302497 7/1984 Fed. Rep. of Germany .

OTHER PUBLICATIONS

Tul'chinskaya et al., Chemical Abstracts, vol. 101, 37923h (1984).
Tishler et al., "Journal of American Chemical Society", vol. 69, (1947), pp. 1487–1492.
Korte et al., Liebigs Ann. Chem. 615, (1958), pp. 94–99.
Berezowski, J. of Gen. Chem. USSR, vol. 31, No. 10, pp. 3444–3448, (1961).
"Ullmanns Encyclopedia of Technical Chemistry 23", Verlag Chemie, Weinheim–Berstr., 4 edition, 1983, p. 666.
"Riboflavin", Plenum Press, New York, 1975, pp. 318–319, (Rivlin).

Primary Examiner—Donald G. Daus
Assistant Examiner—Diana G. Rivers
Attorney, Agent, or Firm—Oblon, Fisher, Spivak, McClelland & Maier

[57] ABSTRACT

An improved process for the preparation of riboflavin by condensation of a 4,5-dimethyl-N-(D)-ribityl-2-phenylazoaniline derivative with barbituric acid in the presence of an acidic condensing agent in an organic solvent, wherein a 4,5-dimethyl-N-(D)-ribityl-2-(o-alkoxyphenylazo)-aniline of the formula IIa

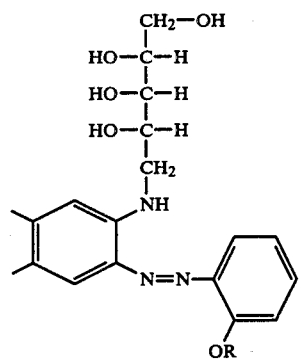

where R is alkyl of 1 to 4 carbon atoms, in particular methyl, is reacted with barbituric acid, as well as the novel intermediates of the formula IIa.

4 Claims, No Drawings

PREPARATION OF RIBOFLAVIN, AND 4,5-DIMETHYL-N-(D)-RIBITYL-2-(O-ALKOXY-PHENYLAZO)-ANILINE INTERMEDIATES

The present invention relates to an improved process for the preparation of riboflavin (I; vitamin $B_2$) by condensation of a 4,5-dimethyl-N-(D)-ribityl-2-phenylazoaniline derivative (II) with barbituric acid (III) in the presence of an acidic condensing agent in an organic solvent, and furthermore relates to a 4,5-dimethyl-N-(D)-ribityl-2-(o-alkoxyphenylazo)-anilines of the formula IIa

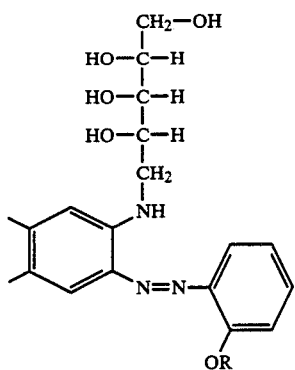

where R is alkyl of 1 to 4 carbon atoms, in particular methyl.

Surprisingly, the compounds of the formula IIa permit the process described above to be carried out in a more advantageous manner.

Apart from the improvement according to the invention, this final step in the synthesis of riboflavin is disclosed in a number of publications. The reaction of II with III to give I was first described in J. Am. Chem. Soc. 69 (1947), page 1487 et seq. This publication states, as the reaction medium, in particular a mixture of glacila acetic and dioxane. Since large amounts of the relatively expensive solvent dioxane have to be used in this process, and furthermore dioxane is dangerous to health and therefore unaccaptable, this process is unsuitable for the production of riboflavin on an industrial scale.

A detailed investigation into the suitability of various organic acids as catalysts for the reaction of II with III has been described by Berezowski et al. in J. Gen. Chem. USSR 31 (1961), page 3444 et seq. Boiling butanol was used as the solvent. The yields of not more than about 70% which were obtained are unsatisfactory for an industrial-scale process, especially when the procedure in question is the final reaction step of a multi-stage process and these yields are furthermore obtained only with the use of a fairly large excess of III.

According to Czechoslovakian Pat. No. 127,303, II is reacted with III in the presence of glacial acetic acid in butanol or dioxane. The yields achieved are not more than 78%.

Japanese Preliminary Published Application No. 7737/1963 discloses the reaction of II with III in a mixture of alkanols, having boiling points of from 80° to 120° C., and glacial acetic acid over $Al_2O_3$ or purified diatomaceous earth. The yields are 67–69% of theory.

Japanese Preliminary Published Application No. 10151 furthermore discloses a process for the condensation of II with III in a mixture of a solvent, such as ethyl acetate, and nitrobenzene or a nitroalkane. The yields are 82–84%. The disadvantages of this process are that the space-time yields are too low and nitrobenzene or the like, which has a very high vapor pressure and is extremely toxic, has to be present.

Czechoslovakian Pat. No. 195,229 discloses a process for the preparation of I from II and III in a mixture of xylene, a $C_3$–$C_5$-alkanol, glacial acetic acid and acetates. The yields are 86–87.4% of a relatively pure I. The disadvantages of this process are the expensive working up procedure for the solvent mixture used, the poor space-time yields and the difficulties in filtering off the product, since I is obtained from this mixture in the form of relatively small crystals which are difficult to filter.

Furthermore, Japanese Preliminary Published Application No. 3575/1957 discloses a process for the preparation of I by reacting II with III in a mixture of an organic solvent and glacial acetic acid over an acidic salt, such as $SnCl_2$, $ZnCl_2$, $FeCl_2$, $AlCl_3$ or $BiCl_3$, as a catalyst. The resulting yields of I are higher than 80% of theory. The disadvantages of this process are that the good yields stated are achieved only if barbituric acid is used in an excess of from 75 to 110%, the riboflavin obtained must in any case be subjected to subsequent purification involving losses of yield, and the regeneration of the solvent and of the metal salts is very time-consuming and expensive.

It is an object of the present invention to overcome the disadvantages of the prior art in the final step of the riboflavin synthesis described above, ie. to make it possible to carry out this step in a simple manner, in a shorter time and with better yields and still obtain very pure riboflavin.

In the condensation to give riboflavin, the azo component usually employed is a compound of the formula II in which the phenyl ring of the phenylazo group is unsubstituted.

In contrast, in the process described in U.S. Pat. No. 2,350,376, a compound II which is substituted in the phenyl ring of the phenylazo group, ie. 4,5-dimethyl-N-(D)-ribityl-2-(p-nitrophenylazo)-aniline, is condensed with barbituric acid.

In J. Am. Chem. Soc. 69 (1947) page 1487 et seq., the dependence of the riboflavin yield on the substituents $R^1$ and $R^2$ in the azo compound of the general formula IV is investigated.

$$
\begin{array}{c}
CH_2-OH \\
HO-C-H \\
HO-C-H \\
HO-C-H \\
CH_2 \\
NH
\end{array}
\quad (IV)
$$

| IV | $R^1$ | $R^2$ |
|---|---|---|
| a | H | H |
| b | $NO_2$ | H |
| c | H | $NO_2$ |
| d | Cl | H |
| e | H | Cl |

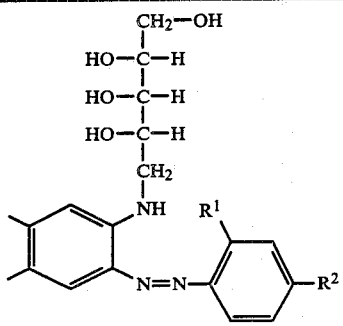

| IV | R¹ | R² |
|---|---|---|
| f | H | OCH₃ |
| g | H | COOH |
| h | H | CH₃ |
| i | CH₃ | H |

It was found that the best riboflavin yields were achieved with Iva, where $R^1$ and $R^2$ are each H. Slightly poorer yields were obtained starting from Ivb and Ivc, while Ivd, e and f gave substantially poorer yields. The differences in the riboflavin yields as a function of $R^1$ and $R^2$ proved to be substantially more pronounced when the corresponding tetraacetyl compounds Va–f were used.

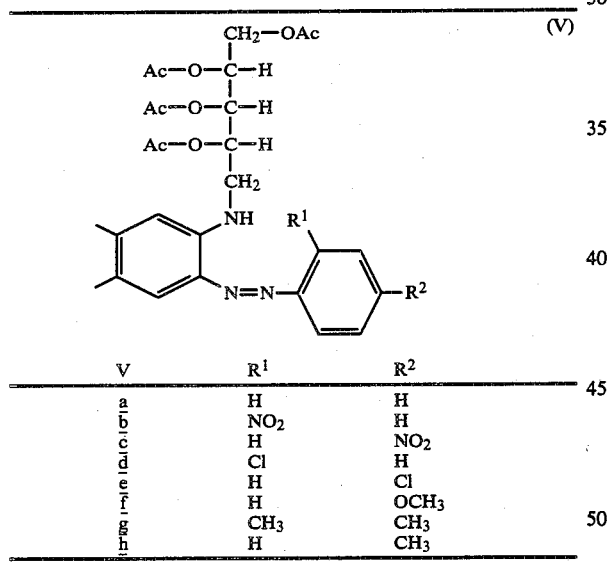

| V | R¹ | R² |
|---|---|---|
| a | H | H |
| b | NO₂ | H |
| c | H | NO₂ |
| d | Cl | H |
| e | H | Cl |
| f | H | OCH₃ |
| g | CH₃ | CH₃ |
| h | H | CH₃ |

Here, it is possible to recognize a clear dependence of the yield on the substitution at the phenyl ring of the phenylazo group, this dependence being as follows: Vc(p—NO₂)>Vb(o—NO₂)>Va(unsubstituted)>Ve(p—Cl)>Vd(o—Cl)>Vf(p—OCH₃).

According to Liebigs Ann. Chem. 615 (1958) page 94 et seq., the yield of I was increased by about 15%, to about 61%, by using the azo compound IVg instead of IVh.

All these findings show that the yield of riboflavin increases when substituents having a —M effect (COOH, NO₂) are introduced into the phenylazo group, whereas in the case of substituents having a +M effect (Cl, OCH₃) it decreases substantially compared with the unsubstituted aromatic. There is also a steric effect: with the exception of Ivb, o-substitution products lead to substantially lower yields than the corresponding p-substitution products. These findings were confirmed in the series of experiments which we have carried out, and which is summarized as Comparative Example 1.

According to J. Am. Chem. Soc. 69 (loc. cit.), the p—NO₂ derivative Vc gives the best riboflavin yields. In order to synthesize Vc, however, the tetraacetyl compound VI must first be synthesized and then coupled to a p-nitrophenyldiazonium salt. After condensation with barbituric acid, the 4 acetyl groups must then be eliminated in an additional stage in order to obtain riboflavin.

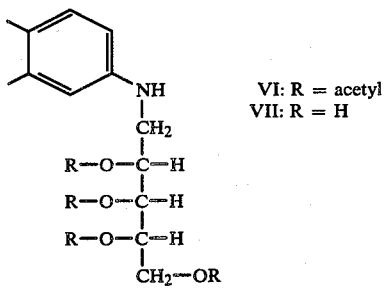

VI: R = acetyl
VII: R = H

Direct coupling of the non-acetylated compound 3,4-dimethyl-N-ribitylaniline (VII) to a p-nitrophenyldiazonium salt did not give a pure product since the amount of the isomer VIII (VIIIa in this case), which is useless for the preparation of I, was particularly high when this diazonium salt was used.

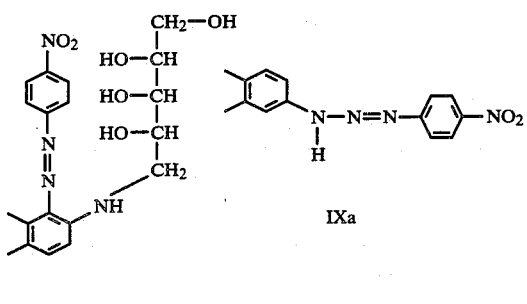

VIIIa

Moreover, coupling of aromatic amines to diazonium salts containing few electrons, eg. p-nitrophenyldiazonium salts, tends to result in the formation of triazenes of the type Ixa, which are impurities which are difficult to remove.

The literature described above thus shows that substituents producing a +M effect, and ortho-substitution in the phenyl ring of the azo component, lead to a reduction in the riboflavin yield.

We have found that this object is achieved and that, particularly surprisingly, especially good yields are obtained using the azo compound IIa which is substituted in the o-position by a low alkoxy group and has not been described in the literature to date (cf. Example 1 and Comparative Examples 1a to 1f). Furthermore, the rate of formation of riboflavin is substantially higher when IIa is used than when the other azo compounds are employed (cf. Example 2 and Comparative Examples 2a to 2f).

Another advantage of using the novel 4,5-dimethyl-N-(D)-ribityl-2-(o-alkoxyphenylazo)-anilines of the formula IIa is evident from the facts below:

As stated above, the reaction of VII with phenyldiazonium salts usually gives not only the unsubstituted or substituted azo compounds of the formula II which are desirable for the preparation of I but also produces the isomers VIII which are useless for the preparation of I,

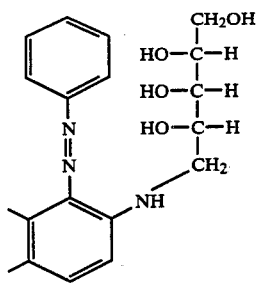

so that the azo compound employed for the condensation with III is actually a mixture of unsubstituted or substituted II and VIII (cf. Ullmanns Encyklopadie der technischen Chemie, volume 23, Verlag Chemie, Weinheim, Bergstrasse, 4th edition, 1983, page 666).

Since the compound VIII present in II forms isoriboflavin X

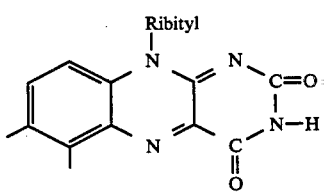

during the condensation with barbituric acid, and the isoriboflavin is difficult to separate off on the one hand and has an adverse effect on the action of the riboflavin on the other hand (cf. Rivlin, Riboflavin, Plenum Press New York, N.Y., 1975, pages 318–319), it is very important with regard to an industrial riboflavin synthesis to keep the content of VIII in II very low.

Surprisingly, the reaction of VII with o-alkoxyanilinediazonium salts gives the azo compounds IIa in the form of virtually pure isomers which contain only traces (1–2%) of the undesired isomer; consequently, virtually no isoriboflavin is formed in the subsequent condensation, which takes place more slowly in the case of the undesired isomer.

The present invention therefore relates not only to the 4,5-dimethyl-N-(D)-ribityl-2-(o-alkoxyphenylazo)-anilines of the formula IIa, but also to a process for the preparation of riboflavin of the formula I

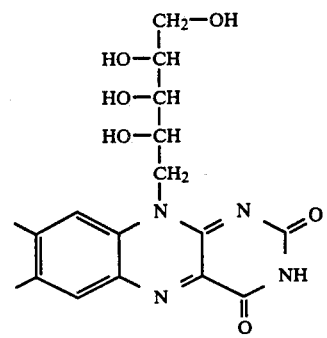

by condensation of a 4,5-dimethyl-N-(D)-ribityl-2-phenylazoaniline of the formula II

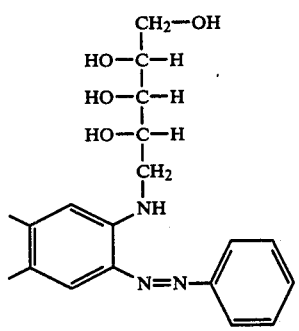

where the phenyl ring of the phenylazo group can be substituted in the ortho- or para-position, with barbituric acid of the formula III

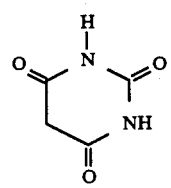

in the presence of an acidic condensing agent in an organic solvent, wherein a 4,5-dimethyl-N-(D)-ribityl-2-(o-alkoxyphenylazo)-aniline of the formula IIa

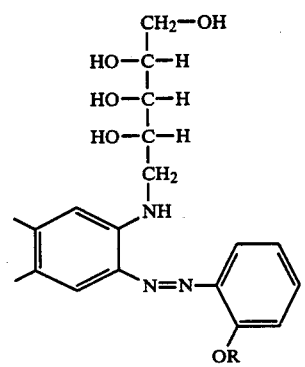

where R is alkyl or 1 to 4 carbon atoms, in particular methyl, is reacted with barbituric acid.

The novel 4,5-dimethyl-N-(D)-ribityl-2-(o-alkoxyphenylazo)-anilines of the formula IIa which are used as starting compounds for the novel process are obtained in a conventional manner by reacting 3,4-dimethyl-N-ribitylaniline with a solution obtained from o-alkoxyaniline with sodium nitrite in a solution containing HCl or sulfuric acid (cf. Example 4).

Advantageously, the novel reaction of a compound of the formula IIa with III is carried out in the presence of an inert diluent or solvent, this also being the conventional procedure to date. Preferred solvents are those in which the water formed during the condensation is also completely or partially soluble, ie. dioxane, tetrahydrofuran, dimethylformamide and especially the relatively cheap lower alcohols having a boiling point of fron 80° to 150° C., such as propanol, isopropanol, n-butanol, isobutanol, and n-pentanol. The most recent, unpublished results show that other particularly suitable solvents are acetates, polyhydric aliphatic alcohols, such as ethylene glycol diacetate, butane-1,4-diol diacetate or glycerol triacetate, alkoxyalkanol acetates, such as 2-ethoxyethyl acetate, and even alkoxyalkanols, such as 1-methoxypropan-2-ol. Ethylene glycol diacetate, 1-methoxypropan-2-ol or a mixture of these is particularly advantageously used. The amount of the solvent is in general about 2–12 liters per kg of II.

Suitable acidic condensing agents are in principle any acids which have been described to date in the literature as being suitable for this reaction, preferably weak organic acids, such as glacial acetic acid, propionic acid, phenylacetic acid, benzoic acid, trimethylacetic acid (pivalic acid), 2,2-dimethylbutanoic acid, 2,2-dimethylpentanoic acid and 1-methylcyclopentanecarboxylic acid.

On the basis of very recent, unpublished discoveries, of particular industrial importance are glacial acetic acid, which is particularly cheap, and commercially available mixtures of synthetic acids which essentially contain saturated tertiary carboxylic acids, in particular Versatic ®-10-acid, a synthetic $C_{10}$-carboxylic acid from Shell Chemie, and similar products from Esso, which are commercially available under the name neo acids. Examples of these are neopentanoic acid, which contains trimethylacetic acid as the main component, and neodecanoic acid, which is probably similar to Versatic-10-acid in its composition.

The amount of the carboxylic acid is preferably about 0.5–6 moles per mole of IIa, corresponding to, for example, from about 0.08 to 1 kg per kg of IIa in the case of glacial acetic acid, and 0.2–2.7 kg per kg of IIa in the case of Versatic-10-acid.

A particular advantage of the novel process is that the yields obtained are substantially higher than previously even when equimolar amounts of IIa and III are used. These yields are about 85%, but can be further increased to well above 90% if III is used in as much as a 0.3 molar excess. A larger excess does not cause problems but does not result in any further noticeable increase in yield.

The reaction temperatures are 80°–120° C. The reaction is preferably carried out at above 100° C., ie. about 100°–115° C., and in an appropriately high-boiling solvent.

The reaction mixture can be worked up by a conventional method, for example by leaving it to cool and filtering off the riboflavin which has crystallized out.

In the condensation with barbituric acid, the novel 4,5-dimethyl-N-(D)-ribityl-2-(o-alkoxyphenylazo)-anilines IIa form very pure riboflavin in shorter reaction times and better yields compared with those obtained using unsubstituted or differently substituted azo compounds of the general formula IV.

EXAMPLE 1 AND COMPARATIVE EXAMPLES 1a TO 1f 25 millimoles of each of the azo compounds of the general formula IV

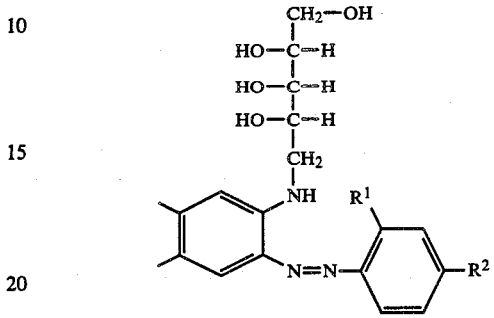

which are shown in Table 1 below (isomer mixtures containing from 90 to 97% of the isomer IV were employed; all amounts are based on the amount of isomer IV used) were refluxed with 3.20 g (25 millimoles) of barbituric acid in a mixture of 100 ml of dioxane and 15 ml of pivalic acid for 16 hours (h). Thereafter, the reaction mixture was cooled to room temperature (RT), and the precipitated riboflavin crystals were filtered off under suction, washed with twice 50 ml of methanol at RT, with twice 80 ml of water at 80° C. and again with twice 50 ml of methanol at RT, and finally dried overnight under reduced pressure at 70° C. The results are shown in the table below. The purity of the riboflavin was determined by UV measurement in accordance with Pharmacopeia Europa.

TABLE 1

| | Starting compound IV | | Yield | Yield [% of | Purity |
|---|---|---|---|---|---|
| | $R^1$ | $R^2$ | [g] | theory] | [%] |
| Example 1 | —O—CH$_3$ | H | 7.87 | 83.7 | 96.1 |
| Comparative Example | | | | | |
| 1a | H | H | 6.56 | 69.8 | 97.7 |
| 1b | H | —CH$_3$ | 6.44 | 68.5 | 97.2 |
| 1c | —CH$_3$ | H | 5.20 | 55.3 | 86.2 |
| 1d | H | —Cl | 5.19 | 55.2 | 92.3 |
| 1e | Cl | H | 4.63 | 49.3 | 90.7 |
| 1f | H | —O—CH$_3$ | 3.72 | 39.6 | 88.0 |

It should furthermore be noted that, under the conditions of Example 1, the yield of riboflavin was 70% after only 4 hours and the conversion was virtually complete after 10 hours, whereas in the comparative experiments 1a to 1f the stated yields were achieved only after 16 hours.

EXAMPLE 2 AND COMPARATIVE EXAMPLES 2a TO 2f 25 millimoles of each of the azo compounds of the formula IV which are shown in Table 2 below were refluxed with 3.20 g (25 millimoles) of barbituric acid in a mixture of 100 ml of dioxane and 15 ml of pivalic acid. The reactions mixtures were cooled to RT after 2, 4, 7, 10 and 16 hours in each case and worked up as described in Example 1, and the yields shown in Table 2 were calculated from the amounts of riboflavin obtained. The purity of the resulting riboflavin samples corresponded roughly to the purities stated in Example 1 or Comparative Examples 1a to 1f.

water, and dried at +70° C. under reduced pressure. The yield was 109.5 g (72.2% of theory) of riboflavin of melting point 142°-144° C. Only one isomer was detect-

|  | Starting compound IV | | Yield [%] as a function of time (h), after | | | | |
| --- | --- | --- | --- | --- | --- | --- | --- |
|  | $R^1$ | $R^2$ | 2 h | 4 h | 7 h | 10 h | 16 h |
| Example 2 | —O—CH$_3$ | H | 58.5 | 70.5 | 78 | 80.5 | 82 |
| Comparative Example |  |  |  |  |  |  |  |
| 2a | H | H | 29.5 | 43 | 54.5 | 62 | 70 |
| 2b | H | —CH$_3$ | 27 | 41 | 53 | 61 | 68 |
| 2c | —CH$_3$ | H | 12.5 | 25 | 37 | 47 | 55 |
| 2d | H | Cl | 12.5 | 26 | 38 | 45.5 | 55 |
| 2e | Cl | H | 10 | 23 | 32.5 | 41 | 49 |
| 2f | H | —O—CH$_3$ | 0.5 | 2 | 5 | 20 | 40 |

EXAMPLE 3

10.0 g of 97% pure 4,5-dimethyl-N-(D)-ribityl-2-(o-methoxyphenylazo)-aniline (corresponding to 0.0249 mole) were refluxed with 3.84 g (0.03 mole) of barbituric acid in a mixture of 40 ml of isobutanol, 7 ml of isobutyl acetate and 4.7 ml of glacial acetic acid for 10 h, after which the reaction mixture was cooled to RT, and the crystals formed were filtered off under suction, washed with cold methanol and water at 80° C., and dried at 70° C. under reduced pressure. The yield was 8.2 g, corresponding to 87.6% of theory, and the purity was 94% of theory (Phar. Europ.).

COMPARATIVE EXAMPLE 3

20.0 g of 87% pure 4,5-dimethyl-N-(D)-ribityl-2-phenylazoaniline (corresponding to 0.0485 mole) were refluxed with 7.26 g (0.0567 mole) of barbituric acid in a mixture of 80 ml of isobutanol, 14 ml of isobutyl acetate and 10 ml of glacial acetic acid for 10 h. Working up as described in Example 3 gave 15.4 g (84.5% of theory) of riboflavin having a purity of 93.8% (Pharm. Europ.).

EXAMPLE 4

Preparation of
4,5-dimethyl-N-(D)-ribityl-2-(o-methoxyphenylazo)-aniline (a) 58.6 g (0.476 mole) of o-methoxyaniline were dissolved in 140 ml of water, 118 ml of concentrated hydrochloric acid were added to the solution, the mixture was cooled to 0° C. and a solution of 33 g of sodium nitrite in 100 ml of water was added dropwise a from 0° to 5° C.

(b) 100 g (0.39 millimole) of 3,4-dimethyl-N-(D)-ribitylaniline were dissolved in 400 ml of 1N hydrochloric acid, and the solution was brought to pH 3 by means of 30% strength aqueous sodium formate solution and then added dropwise, in the course of 1 h, to the diazonium salt solution prepared as described under 2a. The mixture was stirred for a further 3 h at RT and for 30 minutes at 5° C., the crystals formed were filtered off under suction, and the filter cake was washed with 4 times 500 ml of water at 80° C. A sample of the water-moist filter cake was dried and the NMR spectrum showed that the isomeric azo compounds were present in a ratio of 98:2. The major part was dissolved in 350 ml of ethanol, 400 ml of water were added to the hot solution, and the mixture was left to stand overnight. The crystals formed were filtered off under suction, washed with 250 ml of a 1:1 mixture of ethanol and able in the NMR spectrum.

EXAMPLE 5

10.8 g of 97% pure 4,5-dimethyl-N-(D)-ribityl-2-(o-methoxyphenylazo)-aniline (corresponding to 0.0269 mole) and 4.4 g of barbituric acid in a mixture of 35 ml of dioxane and 25 ml of Versatic ®-10-acid were refluxed for 9 h while stirring. The reaction mixture was cooled to RT, and the crystals formed were filtered off under suction, washed with twice 25 ml of methanol, with 3 times 60 ml of water at 80° C. and again with twice 25 ml of methanol, and dried overnight at +70° C. under reduced pressure. The yield was 9.46 g (93.5% of theory) of riboflavin having a purity of 94.7% (Pharm. Europ.).

EXAMPLE 6

10.8 g of 97% pure 4,5-dimethyl-N-(D)-ribityl-2-(o-methoxyphenylazo)-aniline (corresponding to 0.0269 mole) and 4.4 g of barbituric acid in a mixture of 40 ml of 1-methoxypropan-2-ol and Versatic ®-10-acid were stirred for 9 h at 120° C. Working up as described in Example 5 gave 9.46 g (93.5% of theory) of riboflavin having a purity of 92.2% (Pharm. Europ.).

EXAMPLE 7

10.8 g of 97% pure 4,5-dimethyl-N-(D)-ribityl-2-(o-methoxyphenylazo)-aniline (corresponding to 0.0269 mole) and 4.4 g of barbituric acid in a mixture of 50 ml of isobutanol and 25 ml of Versatic ®-10-acid were refluxed for 9 h while stirring, after which the reaction mixture was cooled to RT, and the crystals formed were filtered off under suction, washed with twice 20 ml of isobutanol, with twice 25 ml of methanol and with 3 times 60 ml of water at 80° C. and dried overnight at +70° C. under reduced pressure. The yield was 9.73 g (96.2% of theory) of riboflavin having a purity of 94.6% (Pharm. Europ.).

We claim:
1. An improved process for the preparation of riboflavin of the formula I wherein a 4,5-dimethyl-N-(D)-ribityl-2-(o-alkoxy-

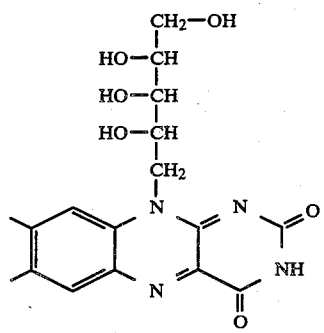

(I)

phenylazo)-aniline of the formula IIa

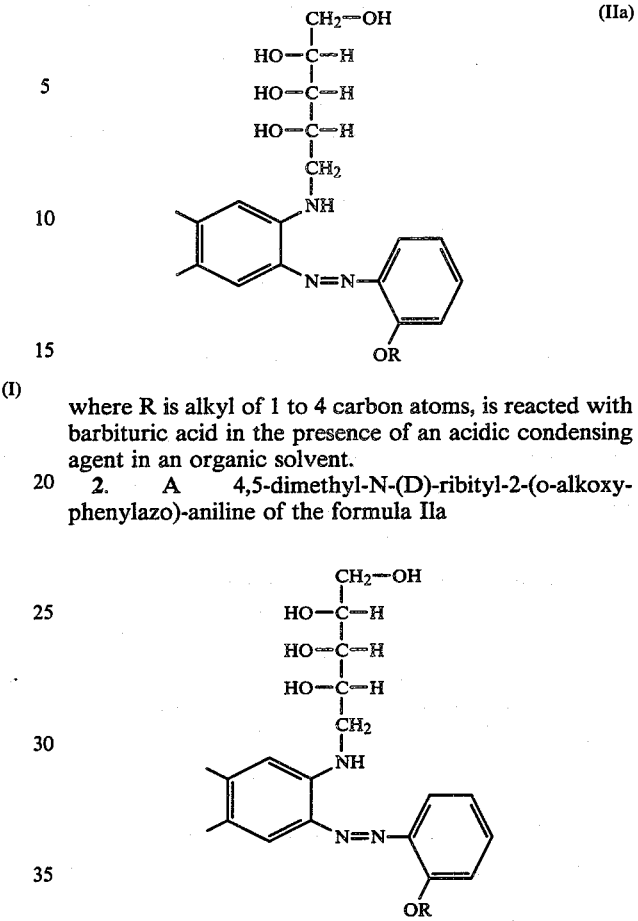

where R is alkyl of 1 to 4 carbon atoms, is reacted with barbituric acid in the presence of an acidic condensing agent in an organic solvent.

2. A 4,5-dimethyl-N-(D)-ribityl-2-(o-alkoxyphenylazo)-aniline of the formula IIa where R is alkyl of 1 to 4 carbon atoms.

3. 4,5-Dimethyl-N-(D)-ribityl-2-(o-methoxyphenylazo)-aniline.

4. A process according to claim 1 wherein the 4,5-dimethyl-N-(D)-ribityl-2-(o-alkoxyphenylazo)-aniline is 4,5-dimethyl-N-(D)-ribityl-2-(o-methoxyphenylazo)-aniline.

* * * * *